United States Patent
Zipprich

(10) Patent No.: US 9,629,699 B2
(45) Date of Patent: Apr. 25, 2017

(54) TREATMENT ELEMENT FOR USE WITH A DENTAL-IMPLANT PART, TREATMENT SYSTEM AND METHOD FOR CLEANING A DENTAL-IMPLANT PART

(71) Applicants: Urs Brodbeck, Erlenbach (DE); Markus Schlee, Forchheim (DE); Holger Zipprich, Malchen (DE)

(72) Inventor: Holger Zipprich, Malchen (DE)

(73) Assignee: ZYFOMA GMBH, Weiterstadt (DE)

( * ) Notice: Subject to any disclaimer, the term of this patent is extended or adjusted under 35 U.S.C. 154(b) by 0 days.

(21) Appl. No.: 14/440,012

(22) PCT Filed: Oct. 18, 2013

(86) PCT No.: PCT/EP2013/003150
§ 371 (c)(1),
(2) Date: Apr. 30, 2015

(87) PCT Pub. No.: WO2014/075755
PCT Pub. Date: May 22, 2014

(65) Prior Publication Data
US 2015/0282907 A1 Oct. 8, 2015

(30) Foreign Application Priority Data

Nov. 14, 2012 (DE) .......... 10 2012 022 227
Nov. 14, 2012 (DE) .......... 10 2012 022 593
Feb. 5, 2013 (DE) .......... 10 2013 201 883

(51) Int. Cl.
A61C 3/00 (2006.01)
A61C 17/00 (2006.01)
(Continued)

(52) U.S. Cl.
CPC ............ *A61C 17/00* (2013.01); *A61C 8/0093* (2013.01); *A61C 17/02* (2013.01); *A61C 19/063* (2013.01);
(Continued)

(58) Field of Classification Search
CPC ....... A61C 17/00; A61C 8/093; A61C 19/002; A61C 19/02; A61C 17/02; A61C 19/063;
(Continued)

(56) References Cited

U.S. PATENT DOCUMENTS 3,420,760 A 1/1969 Freedman et al.
4,124,522 A 11/1978 Barton
(Continued)

FOREIGN PATENT DOCUMENTS

CH 698 841 11/2009
CN 1921807 A 2/2007
(Continued)

OTHER PUBLICATIONS

International Search Report issued by the European Patent Office in International Application PCT/EP2013/003150 on Jan. 28, 2014.
(Continued)

*Primary Examiner* — Heidi M Eide
(74) *Attorney, Agent, or Firm* — Henry M. Feiereisen LLC

(57) ABSTRACT

A treatment element for use with a dental-implant part anchored in a patient's jawbone is disclosed, wherein the treatment element includes a base body having a connection system adapted to the dental-implant part for mechanical connection of the base body with the dental-implant part, and at least one media duct for conducting a cleaning liquid.

11 Claims, 6 Drawing Sheets

(51) Int. Cl.
*A61C 8/00* (2006.01)
*A61N 1/05* (2006.01)
*A61C 17/02* (2006.01)
*A61C 19/06* (2006.01)
*A61C 8/02* (2006.01)

(52) U.S. Cl.
CPC .......... *A61N 1/0548* (2013.01); *A61C 8/0007* (2013.01); *A61C 8/0089* (2013.01)

(58) Field of Classification Search
CPC .... A61C 8/0007; A61C 8/0089; A61N 1/0548
See application file for complete search history.

(56) References Cited

U.S. PATENT DOCUMENTS

| | | | |
|---|---|---|---|
| 5,089,606 A | 2/1992 | Cole et al. | |
| 5,201,656 A | 4/1993 | Sicurelli et al. | |
| 5,981,454 A | 11/1999 | Small | |
| 2003/0224327 A1* | 12/2003 | Constantino | A61C 8/0089 433/165 |
| 2007/0016163 A1 | 1/2007 | Santini, Jr. et al. | |
| 2008/0118893 A1 | 5/2008 | Armellini et al. | |
| 2009/0029316 A1 | 1/2009 | Dunn | |
| 2010/0291506 A1 | 11/2010 | Olsson et al. | |
| 2011/0029080 A1 | 2/2011 | Gilbert | |
| 2011/0207075 A1 | 8/2011 | Altshuler et al. | |
| 2012/0028215 A1* | 2/2012 | Wade | A61C 8/0089 433/75 |
| 2012/0156645 A1 | 6/2012 | Jacoby | |
| 2012/0196251 A1* | 8/2012 | Taft | A61B 18/1402 433/216 |
| 2013/0166039 A1* | 6/2013 | Shaw-Klein | A61C 8/0007 623/23.49 |

FOREIGN PATENT DOCUMENTS

| | | |
|---|---|---|
| DE | 16 17 156 | 3/1971 |
| DE | 26 00 498 | 7/1976 |
| DE | 197 10 127 | 9/1998 |
| DE | 199 16 153 | 12/2003 |
| DE | 698 16 219 | 4/2004 |
| DE | 102007045210 | 4/2009 |
| DE | 102010018245 | 10/2011 |
| EP | 0 757 547 | 6/1998 |
| EP | 1 772 432 | 4/2007 |
| EP | 2 031 048 | 3/2009 |
| JP | H08-299999 | 11/1996 |
| JP | 2008-214591 | 9/2008 |
| WO | WO 2009/083086 | 7/2009 |
| WO | WO 2010/139762 | 12/2010 |

OTHER PUBLICATIONS

Chanwu Cai: "Electromagnetic Flowmeter", in China Petrochemical Press, Mar. 31, 2004, p. 386.
Chinese Search Report issued by the Chinese Patent Office on Jan. 26, 2017 in counterpart Chinese Application No. 2014800176651.
English translation of Chinese Search Report issued by the Chinese Patent Office on Jan. 26, 2017 in counterpart Chinese Application No. 2014800176651.

* cited by examiner

TREATMENT ELEMENT FOR USE WITH A DENTAL-IMPLANT PART, TREATMENT SYSTEM AND METHOD FOR CLEANING A DENTAL-IMPLANT PART

CROSS-REFERENCES TO RELATED APPLICATIONS

This application is the U.S. National Stage of International Application No. PCT/EP2013/003150, filed Oct. 18, 2013, which designated the United States and has been published as International Publication No. WO 2014/075755 A1 and which claims the priority of German Patent Application, Serial No. 10 2012 022 227.0, filed Nov. 14, 2012, German Patent Application, Serial No. 10 2012 022 593.8, filed Nov. 14, 2012 and German Patent Application, Serial No. 10 2013 201 883.5, filed Feb. 5, 2013 pursuant to 35 U.S.C. 119(a)-(d).

BACKGROUND OF THE INVENTION

The invention relates to a treatment element, in particular for use with a dental-implant part anchored in a patient's jawbone. It also relates to a treatment system with such a treatment element as well as to a method for cleaning a dental-implant part.

To compensate for the loss of a tooth, dental implants can be used within the framework of a reconstructive therapy. Usually, they are inserted into the jawbone in the place of an extracted or shed tooth, in order to fix there, after a healing-in phase of about four to twelve weeks, a prosthetic part or a crown serving as a denture piece. For this purpose, such a dental implant is usually designed as a suitably shaped metallic body, which is inserted in the intended place in the jawbone by screwing it in. As a rule, the apical end of the dental implant is provided with a screw thread, mostly a self-cutting screw thread, with which the dental implant is inserted into the correspondingly prepared implant bed.

In view of the meanwhile relatively high number of implants inserted into the human body, in particular in the dental area, and their relatively long duration of use, it has been noted that the occurrence of biofilm-associated inflammation statuses of the periimplantary tissue is constantly increasing. On the solid surface of the implant, enclosed by tissue and tissue liquid, a biofilm develops, which is colonized by bacteria which may finally lead to chronic and recurrent infections. This syndrome is called periimplantitis. In particular in the dental area, similar to parodontitis, a combination of neglected mouth hygiene, adhesion of a biofilm on the usually microrough surface of the post part, and other factors lead to the full picture of periimplantitis, which is characterized by an increasing charge and destruction of the hard and soft tissues. The areas where the hard and/or soft tissues retreat are usually covered by a biofilm.

Both with and without treatment, a progressing of the periimplantary inflammation may lead to loss of the implant and deterioration of the tissue of the body or bone in the area of the anchoring spot. Therefore, it is desirable to initiate suitable countermeasures as soon as possible after discovering such an inflammation. These measures may range from an optimization of mouth hygiene to therapeutical interventions in the form of surgical measures, i.e. removal of the afflicted implant and new insertion of a replacement implant. However, in particular the last-mentioned measure is a great burden for the tissue as a whole and often entails a massive reduction of tissue in the environment of the place of insertion. Therefore, it is highly desirable to find alternative efficient measures for combating an existing or beginning periimplantitis.

SUMMARY OF THE INVENTION

The invention is, therefore, based on the problem to provide a treatment element for combating or checking a beginning periimplantitis, which can be used already prior to the therapeutical measures properly speaking, possibly making the latter completely superfluous. Furthermore, a treatment system with such a treatment element and a method shall be provided, with which the treatment element can be used in a particularly favorable manner.

With regard to the treatment element, this problem is solved by a treatment element for use with a dental-implant part anchored in a patient's jawbone, said treatment element, including a base body having a connection system adapted to the dental-implant part for mechanical connection of the base body with the dental-implant part, and at least one media duct for conducting a cleaning liquid.

Advantageous embodiments of the invention are the subject matter of the dependent claims.

The invention starts out on the consideration that for an effective and efficient treatment of inflammation phenomena, especially in the environment of an inserted dental implant, therapeutical measures can be avoided or at least be kept at a low extent, by consistently combating at an early stage already the bacterial colonization of the implant and its environment. This should in particular take place already when therapeutical measures are not yet necessary. Such a consistent combat of bacteria colonization should follow two main approaches, namely, on the one hand, an as far-reaching and reliable a killing of bacteria as possible and, on the other hand, a reliable and comprehensive cleaning of the implant material, removing, to a great extent, any adhering organic residues or the like, which might promote the new colonization with bacteria.

Most surprisingly, it has turned out that these two objectives can be followed by a common approach by feeding a suitable cleaning liquid to the afflicted space area in a purposeful and localized manner, for example by using a suitably chosen biocidal liquid or the like. Therefore, the base body of the treatment element is provided with of a number of media ducts for a cleaning liquid.

Preferably, these media ducts are guided and positioned in such a way that it is possible to act upon the area to be cleaned in the inserted dental-implant part at the exact target spot. For this purpose, advantageously the or each media duct includes an outlet opening, positioned from the dental-implant part, with the base body placed on the dental-implant part, at a distance of not more than 10 mm, preferably not more than 5 mm, particularly preferably not more than 3 mm. In an alternative or additional advantageous development, the media duct(s) is/are arranged directly in or on the base body in the manner of an integrated construction.

Surprisingly, it has also turned out that a particularly high cleaning effect can be achieved on the inserted implant part by applying several different cleaning liquids combined with each other or sequentially one after another. To make this possible in a purposeful and need-based manner, the media ducts provided in or on the base body of the treatment element advantageously form a duct system with at least two partial ducts which can be charged with liquid independently of each other. In another advantageous embodiment, at least one backflow duct for returning or sucking off the used cleaning liquid from the area of the place of insertion is additionally provided.

In a particularly advantageous supplement, it is additionally provided to purposefully use electric current as a medium for killing the bacteria and/or cleaning the afflicted implant part. In particular, a reliable removal of any adhering organic material can be achieved by charging the implant part with electric current. In order to make this possible under avoidance of therapeutical interventions, i.e. in particular without surgically removing the inserted implant, it is provided to feed the electric current directly to the afflicted implant part while it is still inserted, i.e. without its prior removal from the bone tissue.

For this purpose, the preferred treatment element is supplied, which is provided, due to its design, for being fixed on the inserted dental-implant part and, consequently, includes connection means which are suitably adapted to the inserted dental-implant part. The treatment element is advantageously designed for producing the current flow provided for cleaning the inserted implant part in a purposefully localized manner in the immediately adjacent space area. In particular, it is in this connection provided, as a design principle for the treatment element, to supply means for guiding a current flow, with which the electric current can be fed to the inserted implant part, whose inserted area, in particular the insertion area in the bone tissue, provided with the thread, can be used as an electrode. To form an opposite pole or the counterelectrode, it is additionally provided to suitably position a contact surface or an electric contact point in the immediate vicinity. The before-mentioned components should be positioned and possibly suitably connected with a current source in such a way that the electric current applied for the purpose of treatment and cleaning can flow through the surface zone of the inserted implant part afflicted by the bacteria and, from there, as directly as possible, i.e. in particular without making any "detours" through further body tissue or the like, to the contact surface or contact point.

For this purpose, the treatment element advantageously comprises suitably chosen and positioned conduction elements, which, for their part, can be connected to a suitably chosen current or voltage source. Due to the design, it is provided, among others, to establish an electrically conductive connection to the inserted implant part via one of the conduction elements, so that the desired current flow through the inserted implant part can take place and the latter can form one of the electrodes.

The second conduction element, provided in the manner of a counterelectrode and forming the other contact surface for the current flow, shall preferably be positioned in the immediate spatial vicinity of the inserted implant part. It is, thereby, intended that the current flows through the contact area of the inserted implant part to the surrounding bone tissue or soft tissue and, from there, as directly as possible, to the contact surface, without requiring a current flow through excessively large areas of the body tissue. For this purpose, the second conduction element is preferably shaped geometrically in such a way that an "electrically active" zone develops, which is localized to a great extent near the place of insertion, for example in the form of a needle-like or wire-like shape. In an alternative or additional advantageous development, the second conduction element is arranged in or on the base body of the treatment element, in the manner of an integrated embodiment, for example in the form of an electrode body.

The conduction elements can be designed, in the manner of "conventional" electrodes, as suitably chosen and geometrically configured electrodes, for example based on metal in the form of metallic wires or the like. In this case, the electrode forming the second conduction element is preferably provided with an electric insulation, for example as a plastic-coated wire, it being possible, for forming the contact or the contact surface, to provide, for example, on the end side a purely metallic area which is not further insulated. Alternatively, however, it is also possible to provide at least one of the conduction elements, preferably the second conduction element, based on the use of the electric conductivity of liquids, for example aqueous solutions of salts or the like. In such cases, the conduction element concerned may also be formed by a number of suitably guided ducts in or on the treatment element, which ducts are charged in use with a suitably chosen electrically conductive liquid, which, for its part, is suitably electrically connected with the current or voltage source, for example via a suitably positioned electrode. The contact or the contact surface for the electric current flow is formed in this case by the end-side exit surface of the respective duct, via which the liquid guided in the duct can get into electric contact with the environment of the duct. This exit surface should, therefore, be suitably positioned, in the above-mentioned sense, in the close vicinity of the inserted implant part.

Dental implants can be designed as so-called single-part implants, whose base body is configured substantially in one piece. However, in order to enable an easier introduction into the patient's mouth and in particular a particularly far-reaching preparation of the prosthesis properly speaking when fixing it to the implant already prior to the treatment of the patient, for example in a dental laboratory, dental implants may also be made up of several parts. In particular, a two-part configuration can be provided, the dental-implant system comprising a first implant part, provided for being anchored in the jawbone, also referred to as the implant properly speaking or post part, and, in addition thereto, an associated second implant part, also referred to as superstructure part or abutment, on which the denture piece intended as a prosthesis or the like can be fastened. The outside of the first implant part or post part is usually provided with a thread, which can be designed as a self-cutting or else as a non-self-cutting thread. Usually, the surface of the area which is to grow into the bone or the bone tissue is roughened or coated.

The superstructure part or abutment is usually screwed together with the post part by means of a suitably chosen connecting screw. When anchoring the abutment, the thread of the connecting screw is screwed into an internal thread in the post part associated therewith. During the screwing-in process, the head of the connecting screw presses the abutment via a counterbore of the abutment onto the post part. In a particularly advantageous embodiment, the treatment element is provided for use for such a two-part or multi-part dental implant. For this purpose, its connection system expediently comprises a connecting screw to be inserted into the screw duct of the post part of a two-part or multi-part dental-implant system. In this embodiment, the treatment element can, therefore, be referred to as a "treatment abutment", which is slipped onto the post part of a multi-part dental-implant system instead of the actually provided abutment of said multi-part dental-implant system.

To obtain with such a structure an electrically particularly reliable and efficient access or contact to the insertion area of the inserted post part, i.e. in particular the latter's metallic base body, the treatment element is designed, in another advantageous embodiment, in such a way that the connecting screw is connected with the first conduction element in an electrically conductive manner.

Advantageously, the base body of the treatment element is electrically insulated on its contact surface to the dental-implant part. This makes sure that the current or potential can be guided in the desired manner, namely with specific inclusion of the inserted area of the dental-implant part into the current guidance. The base body can be designed as such on the basis of an electrically insulating material, for example as a ceramic body or plastic body, it being possible in this case that the electrodes are configured through suitably positioned metallic components or suitably guided liquid ducts. Alternatively, the base body can also be designed as a metallic body, for example made of titanium. In this case, the insulating effect against the dental-implant part can be achieved by attaching a suitable insulating element, in particular an independent component or else a surface coating.

To particularly promote the desired current or potential guidance in the immediate spatial vicinity of the place of insertion of the implant part, the second conduction element of the treatment element is in an advantageous development mounted on the base body so as to be shiftable in a longitudinal direction substantially parallel to the central axis of the base body. In a configuration as an electrode, the latter can be designed in particular as a needle-like element, for example in the form of a thin wire or the like, which after mounting of the treatment element on the dental-implant part can be shifted towards the insertion area. In a configuration as a duct carrying a conductive liquid, a thin pipe, a hollow needle or the like can, for example, be provided instead, which after mounting of the treatment element on the dental-implant part can also be shifted towards the insertion area in such a manner that its exit surface is positioned sufficiently close to the space area of the inserted implant part needing treatment.

In an alternative or additional advantageous development, the second conduction element is fixed on the base body in such a manner that its contact arranged on the end side can be positioned at a distance of maximally 10 mm, preferably of maximally 5 mm, from the central longitudinal axis of the dental-implant part, viewed in lateral direction, and in an additional or further advantageous embodiment, can be positioned at a distance of at least 1 mm, preferably of at least 1.5 mm, from the central longitudinal axis of the dental-implant part, viewed in lateral direction. In this way, the desired generation of relatively high electric current densities directly at the place of insertion of the implant part, with an otherwise low current load on the other body tissue, can be achieved in a particularly favorable way.

As explained above, the conduction elements can be designed in the manner of "conventional" electrodes as suitably chosen and geometrically configured electrodes, for example based on metal. The alternative embodiment based on the use of the electric conductivity of liquids is, however, considered as particularly advantageous, because in this case, on the one hand, a relatively high flexibility of duct guidance and, thus, also for current or potential guidance can be achieved.

With regard to the treatment system for a dental-implant part, the above-mentioned problem is solved with a treatment element of the above-mentioned type, whose conduction elements are electrically connected with a current or voltage source.

It has turned out most surprisingly that a charging of the implant afflicted by bacteria with current or voltage pulses is efficient to a particularly high degree, in particular concerning the removal of organic residues still adhering on the material after the bacteria have been killed. Therefore, the current or voltage source of the treatment system is in a particularly advantageous embodiment configured for a need-based pulsating charging of the conduction elements with a current or voltage. It is particularly preferable to provide an operating voltage applied on the electrodes of up to 30 V.

In order to enable a combination of an electric treatment of the inserted dental-implant part and a liquid-based treatment, which is considered as particularly advantageous, a feeding system for a cleaning liquid or a combination of several cleaning liquids is advantageously connected to the treatment element of the treatment system. It is particularly preferable to provide, as a cleaning liquid, water, mixed with at least one acid and/or at least one salt. It is particularly preferable to provide, as an acid, phosphoric acid, citric acid, formic acid, ethanoic acid, lactic acid, carbonic acid, or a combination thereof. Alternatively or additionally, it is particularly preferable to provide, as a salt, sodium, calcium, aluminium, magnesium, tin, or potassium iodide, chloride, nitrate, carbonate, or hydrogen carbonate and/or ammonium chlorite, nitrate, or iodide, or a combination thereof.

With regard to the method for cleaning a dental-implant part, the above-mentioned problem is solved by applying an electric voltage on the dental-implant part and by rinsing it with a cleaning liquid. Advantageously, the electric voltage is applied in a pulsed manner. In an alternative or additional advantageous development, a cleaning liquid of the above-mentioned type is used.

The advantages achieved with the invention consist in particular in that, through the configuration of the treatment element with the conduction elements, in particular and in a particularly preferred manner, in combination with suitably guided ducts for feeding a cleaning liquid, the dental-implant part can be charged with suitable current or voltage pulses in a purposeful and localized manner, without requiring for this purpose a removal from the patient's mouth or another therapeutical intervention. Thus, in the manner of a preventive or checking measure, bacteria colonies on the inserted implant part can be combated at an early stage, whereby the surprisingly found efficiency of electric currents for killing bacteria, but also for removing any organic material still adhering on the inserted implant body, is utilized.

BRIEF DESCRIPTION OF THE DRAWING

An exemplary embodiment of the invention is explained in detail by means of a drawing, in which FIG. 1, 2 each show a dental-implant system, FIG. 3, 4 each show an implant part or post part of the dental-implant system.

DETAILED DESCRIPTION OF PREFERRED EMBODIMENTS

Identical parts are identified in all figures by the same reference numbers.

Figure 1:
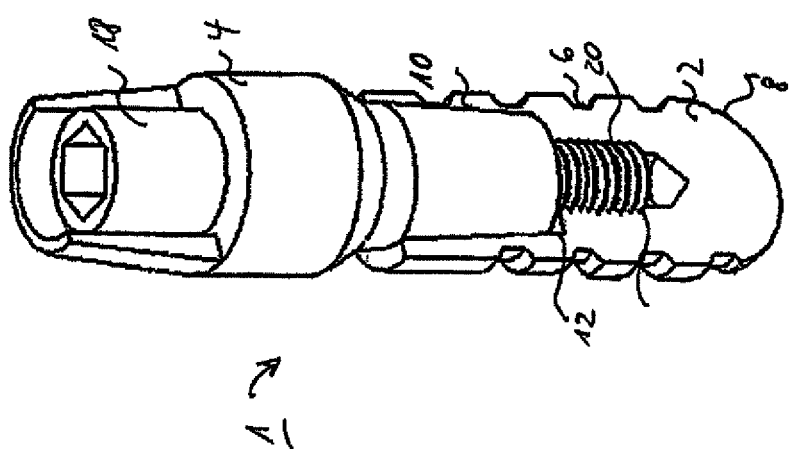
Figure 4:
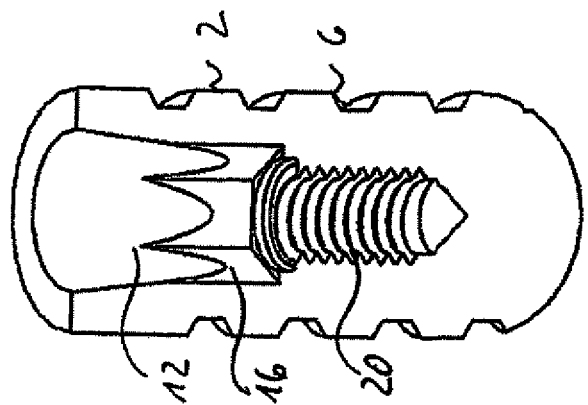

The dental-implant system 1 according to FIG. 1 is intended for use in the jawbone in the place of an extracted or shed tooth, to fix there a prosthetic part or a crown serving as a denture piece. The dental-implant system 1 is made up of several parts and comprises a first implant part 2 configured as a so-called post part, and a second implant part 4, also referred to as superstructure part or abutment, associated therewith and provided for fastening a denture piece. The first implant part 2 or post part is provided on its outside with an external thread 6, configured, in particular at the apical end 8, as a self-cutting screw thread, with which the first implant part 2 or post part can be inserted in the intended place in the jawbone by screwing it in.

Figure 2:
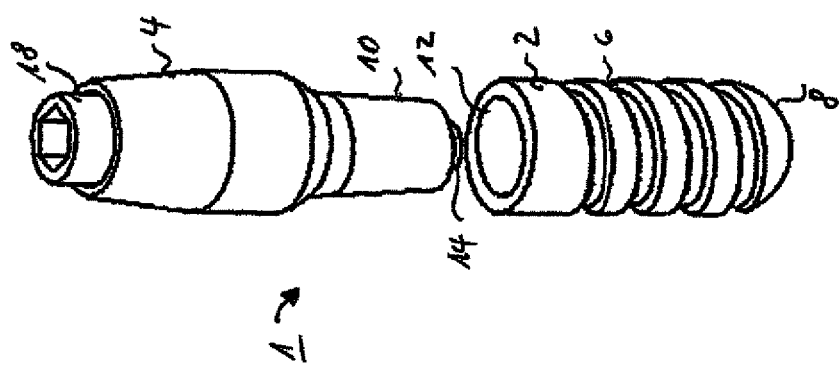
Figure 3:
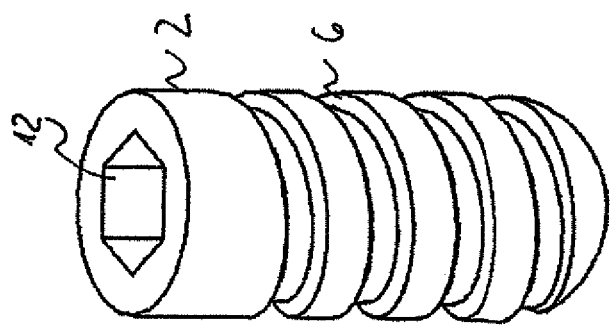

In order to make it possible, after suitably fastening the denture piece or the prosthesis on the abutment or second implant part 4, to anchor it in the post part or first implant part 2 with high mechanical stability, a connection stud 10 is moulded onto the second implant part 4, which connection stud 10 can be pushed into an associated receiving duct 12 provided in the first implant part 2. By pushing the connection stud 10 into the receiving duct 12, the implant parts 2, 4 are mechanically coupled with each other. To ensure a high mechanical stability, the outer contour of the connection stud 10 is adapted to the inner contour of the receiving duct 12, it being possible that both of them are of conical shape, viewed in longitudinal direction (exemplary embodiment according to FIG. 2). Furthermore, as provided in particular in the exemplary embodiment according to FIG. 3, the outer contour of the connection stud 10—and in according adaptation, also the inner contour of the receiving duct 12—can be provided in cross-section with a multiple symmetry (in the exemplary embodiment, a sixtuple symmetry), so that, when joining the above-mentioned components, a rotational locking gear is created and, thus, a reliable rotational orientation of the abutment relative to the post part can be adjusted. In the exemplary embodiment according to FIG. 3, 4, an indexing element 14, whose cross-section also shows a multiple symmetry, is arranged on the end-side of the connection stud 10 for the purpose of an indexing or for creating a rotational locking gear, said indexing element 14 engaging in assembled condition into a corresponding associated duct end piece 16 in the receiving duct 12.

In the exemplary embodiment, the dental-implant system 1 is configured for a screw connection of the implant parts 2, 4 with each other. For this purpose, a connecting screw 18 is provided, which engages into a screw thread 20 provided inside the first implant part 2. With regard to the choice of their materials, the implant parts 2, 4 are suitably adapted to the intended application and are generally made of a ceramic material, such as, for example, zirconium oxide or aluminium oxide, or else of a suitably chosen metal, such as, for example, titanium.

In general, dental-implant systems, in particular also two-part implant systems of the above-described type, present the problem that inflammations or inflammation focuses may arise due to a penetration of bacteria or germs into the tissue area near the place of insertion, in particular in the area of the external thread 6 cut into the jaw. Such inflammations, in particular also as a consequence of a so-called periimplantitis, may lead to a serious deterioration of the tissue and the bone in the area of the place of insertion, especially when they are able to develop and take hold over a long period. Without suitable countermeasures, these deteriorations may lead to the necessity to remove the entire implant system, i.e. in particular also the already inserted post part or second implant part 4, from the bone and replace it by another prosthetics. This most undesirable effect caused by the periimplantitis may, therefore, lead to a total loss of the implant system, so that renewed surgical measures, such as, for example, scraping out the afflicted area in the jawbone and treatment with a new implant system might become necessary. Such a removal may, furthermore, entail a loss of bone or other loss of tissue substance, which in the extreme case may even make a new treatment with another implant completely impossible. Such a necessity of a new treatment caused by a periimplantitis may occur even after relatively long periods after the first insertion of the implant system of, for example, up to several years or even decades.

The germs or bacteria observed in connection with a periimplantitis may in principle colonize the inside of the post part 2, but, as a rule, they preferably adhere directly on the surface of the post part 2 inserted into the jawbone, in the contact area with the surrounding tissue or bone material, i.e. in particular in the area of the external thread 6. In the area of the latter, the surface of the post part 2 can be provided with a roughening or the like, in order to particularly promote the growing-in of the tissue or the bone and to support the healing-in of the post part 2 after its insertion. Especially in the area of such a roughening of the surface, actually considered as particularly favorable for the implant system, however, the colonization of germs or bacteria may take place increasedly, the roughness making a specific removal of the existing germs or bacteria even more difficult.

Therefore, suitable countermeasures are urgently required, in order to be able, in case of a beginning or already existing periimplantitis and under preservation of the already inserted implant system, i.e. in particular of the already inserted post part 2, to efficiently combat the inflammation focus and to kill the germs that have penetrated, so that afterwards, sound tissue or sound bone substance can develop again in the area around the external thread 6. For this purpose, it is desirable, in addition to a specific killing of the germs or bacteria in the afflicted area, to also reliably remove their material residues and fragments from the space area concerned, so that then, the afflicted area can be filled again by sound tissue or bone material and an intimate connection between the outer surface of the post part 2 and the surrounding tissue or bone material can develop again. In addition, the biofilm formed by the bacteria layer, including the organic residues of killed bacteria, should reliably be removed.

For this purpose, i.e. for killing germs or bacteria in the insertion area of the post part 2 and in particular also for subsequently rinsing, removing and carrying away the residues of tissue and material of the killed bacteria, a treatment element 30, 30' is provided, like the one shown in FIG. 5 in a perspective view. A first preferred variant of the treatment system 30 is shown in FIG. 6 in a longitudinal section, a second preferred variant of the treatment system 30' is shown in FIG. 7 in a longitudinal section.

In the exemplary embodiment, the treatment element 30, 30' is designed, due to actually two-part embodiment of the implant system 1, in the manner of a treatment abutment, and is provided for the shown two-part implant system 1 for carrying out the before-mentioned treatment, wherein the treatment abutment 30, 30' should temporarily be placed on the post part 2 in the place of the actual abutment or second implant part 4. Therefore, the following embodiments refer to this case of a two-part implant system 1; but, of course, in an analog embodiment, a corresponding use for single-part implants may also be provided; for this purpose, it would just be necessary to suitably configure the mechanical connection of the treatment element 30, 30' with that part of the implant system which remains in the jawbone during the treatment, for example via a suitable contact surface, with which the treatment element 30, 30' can be placed onto the abutment of the implant in the place of the prosthetics. Alternatively, the treatment element 30, 30' can be placed on top of the actual abutment 4 of the implant system 1, so that a use, for example, for combating an inflammation of the soft tissue (mucositis) through killing of the bacteria and cleaning the surface can be provided, without having to remove the actual abutment 4 for that purpose.

With the two-part embodiment of the implant system 1 provided in the exemplary embodiment, first of all—possibly after removal of the prosthetics fixed on the actual abutment or second implant part 4—the screw connection between the first and second implant parts 2, 4 is detached and the second implant part 4 is taken off, for carrying out the treatment described in detail in the following. The first implant part or post part 2 remains in the jawbone. Then, the treatment abutment 30, 30' is placed onto the post part 2 instead of the actual abutment 4.

Figure 6:
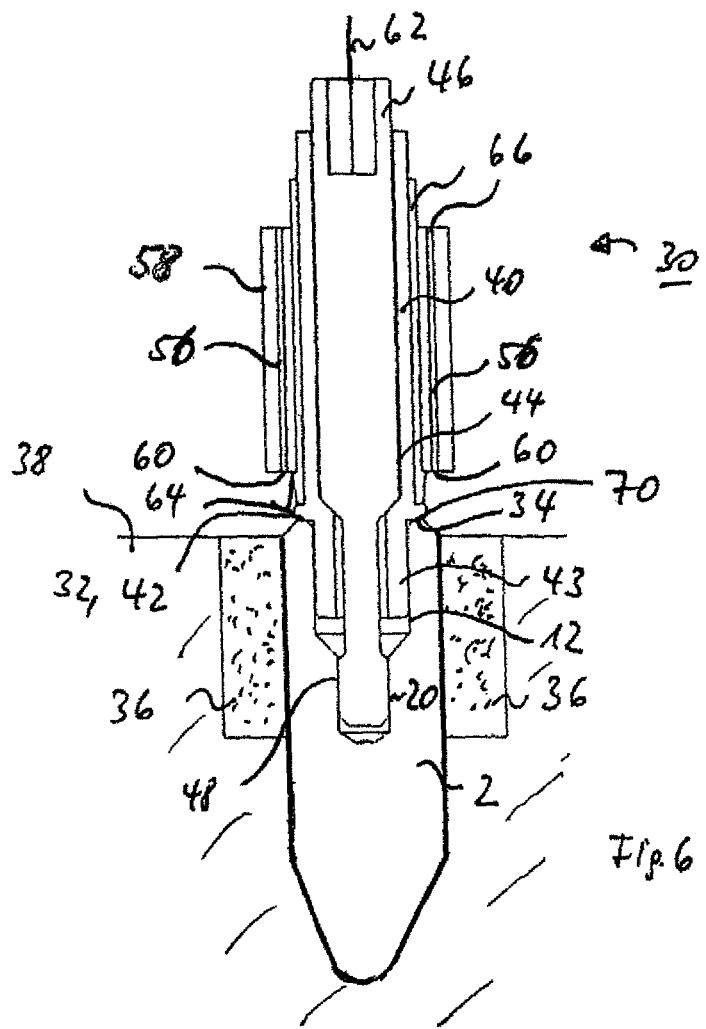
Figure 7:
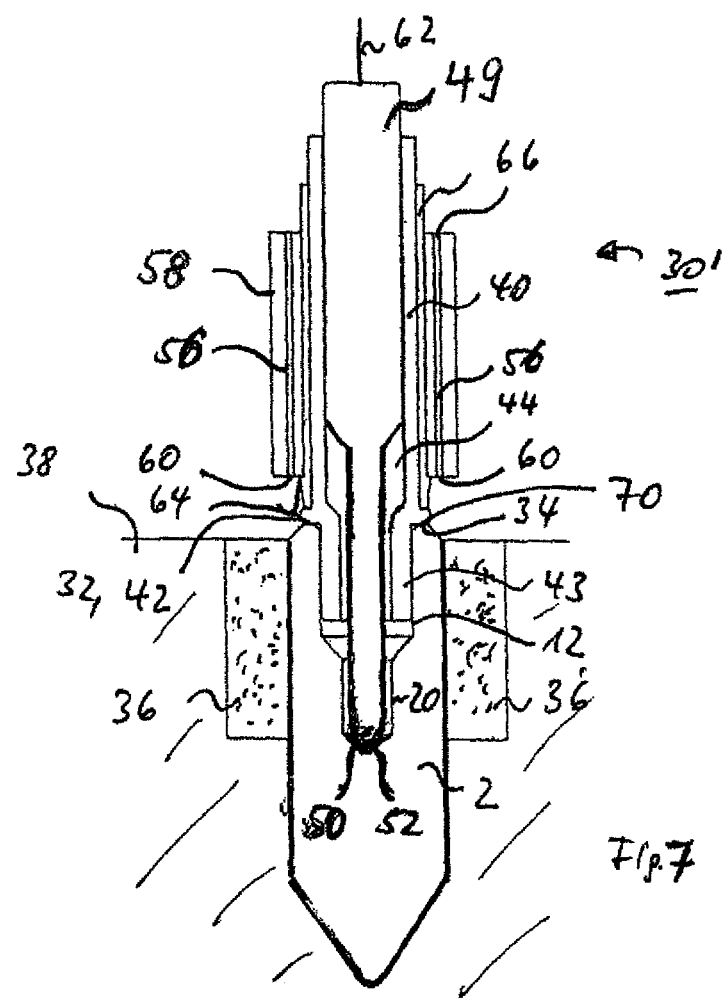

The variants of the treatment element 30, 30' shown in FIGS. 6 and 7 are substantially of identical construction, but differ in the manner in which the fastening on the post part 2 is to be effected during the treatment properly speaking. In the variant according to FIG. 6, a fastening using the screw connection is provided, whereas in the variant according to FIG. 7, it is provided that the treatment element 30, 30' is just slipped onto the post part 2.

Thus, the treatment element 30 shown in FIG. 6 is placed onto the post part 2 and afterwards connected therewith via the screw connection, whereas the treatment element 30' shown in FIG. 7 is slipped into the post part 2 when being placed onto the latter. For this purpose, the treatment implant 30, 30' includes in both variants a substantially planar contact surface 32 auf, with which it can be placed onto the end edge 34 of the post part 2. The contact surface 32 may under certain circumstances also fulfil the function of a sealing face and be designed accordingly; in particular, it can be of a conical design for that purpose.

With regard to its design and fundamental configuration, the treatment abutment 30, 30' is based on two main concepts, each of which is independently considered as inventive: on the one hand, it is designed for specifically killing the germs or bacteria existing in the insertion area of the post part 2 through specifically feeding a cleansing agent or disinfectant which is bactericidal, but tolerated by the human organism. On the other hand, it is designed for removing any residues or fragments of germs and/or bacteria still adhering on the surface of the post part, in particular in the area of the external thread 6, through a pulsed charging with current impulses, from the outer surface of the post part 2, so that such residues can then be washed out.

In a first aspect, which is independently considered as inventive both with regard to the configuration of the system and with regard to the provided steps of the treatment method, the treatment element 30, 30' is, therefore, designed, both structurally and functionally/conceptually, for specifically feeding a treatment liquid for killing the germs or bacteria and/or for cleaning the inserted implant part 2 into the insertion area of the post part 2, in particular the area of the latter's external thread 6. It is particularly preferable to provide, as a treatment liquid, water, mixed with at least one acid and/or at least one salt. It is particularly preferable to provide, as an acid, phosphoric acid, citric acid, formic acid, ethanoic acid, lactic acid, carbonic acid, or a combination thereof. Alternatively or additionally, it is particularly preferable to provide, as a salt, sodium, calcium, aluminium, magnesium, tin, or potassium iodide, chloride, nitrate, carbonate, or hydrogen carbonate and/or ammonium chlorite, nitrate, or iodide, or a combination thereof. The cleaning liquid should be fed in the close vicinity of the treatment element 30, 30' and, thus, in the immediate vicinity of the space area concerned, i.e. the insertion area of the post part 2.

In a second aspect, which is also independently inventive both with regard to the configuration of the system and with regard to the provided steps of the treatment method, the treatment element 30, 30' is designed for reliably detaching the killed bacteria or germs, respectively their residues or fragments, from the outer surface of the post part 2, so that they can then be washed out and, afterwards, sound tissue or bone material can again get into contact with the surface of the post part 2 and the latter can again grow completely into sound tissue or bone material. For detaching the bacteria or germs, respectively their residues or fragments, from the surface, it is provided to wet the latter with a conductive liquid, charging it with pulsed current impulses. It has also turned out most surprisingly that exactly this pulsed charging with current impulses seems to effect the detachment of the bacteria or germs, respectively their residues or fragments, from the surface underneath in a particularly reliable manner, even if said surface is roughened and, in fact, particularly promotes the adhesion of organic material due to its surface structure.

This is based on the surprising discovery that the charging of the post part 2 itself with pulsed current impulses in the area of its outer surface, i.e. in particular in the area of the external thread 6, leads to a separation of fragments of the post material itself, i.e., for example, titanium, from the surface. In particular, the charging with the current impulses, especially with a suitably chosen conductive liquid, for example with ion or acid components, leads to a formation of $TiO_2$ areas, which can then be separated from the titanium surface. Through this separation of surface components from the post part 2, the superficially adhering components or fragments of the germs or bacteria are also detached and completely removed, so that they cannot offer a basis or a nutrient medium for a new colonization of germs in these areas. What remains is a roughened and porous surface, cleaned from germs, bacteria or their components or residues, of the post part 2, which can serve well as a basis for a future integration into the regrowing bone tissue. The remaining surface can also be formed by a titanium-oxide layer, which would also arise when anodizing the surface.

Another promotion of this separation of surface components from the inserted post part 2, which is desirable in the sense of a reliable cleaning of the surface, can be achieved through an advantageous, particularly well suited process guidance during the charging with current. Said process guidance can be such that due to the current flow, an electrolytic formation of gas bubbles takes place in the area of the inserted surface. Here, the post part 2 can be switched anodically or cathodically. In particular in case of an at least temporary cathodic switching of the post part 2, the gases hydrogen, oxygen, nitrogen, and/or carbon dioxide develop through electrolytic induction. The gas bubbles forming thereby rise in the surrounding liquid and thus generate entraining effects, through which the above-mentioned surface components are also removed and discharged towards the outside. It was, for example, most surprisingly observed that, when using a solution containing positive ions, for example, an aqueous saline solution, these ions deposit on the post part 2 when the latter is cathodically switched and, thus, clearly increase the formation of gas bubbles. For example, the presence of Na+ ions in case of a cathodic switching of the post part 2 leads to a considerable formation of gas bubbles, because Na immediately leads to oxidation.

In a third independent inventive aspect, also both with regard to the configuration of the system and with regard to the provided steps of the treatment method, the treatment element 30, 30' is designed for a particularly simple and efficient combination of the before-mentioned aspects. This is based on the concept that both the provided feeding of the cleaning liquid and the specific detachment of the residues and fragments of bacteria and germs can be achieved by applying the above-mentioned current impulses in a common system and, thus, with particularly simple means.

Figure 5:
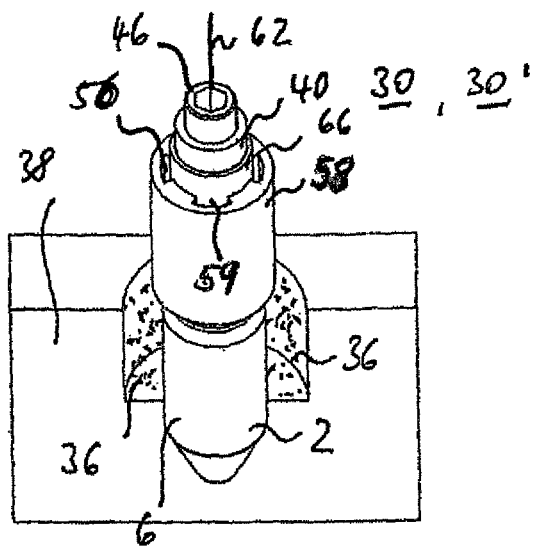
FIG. 5 is a perspective view of a treatment element for a dental-implant part inserted into a patient's jawbone, FIG. 6, 7 each show a longitudinal section of a variant of the treatment element according to FIG. 5, FIG. 8, 9 are each a perspective view of another variant of a treatment element.

In view of these design targets, the treatment element 30, 30' possesses a construction which can be taken from the perspective view according to FIG. 5 and the representation in longitudinal section according to FIGS. 6 and 7, the treatment element 30 30' being in each case represented in the condition mounted on the post part 2. The representations also show a space area 36, surrounding the post part 2 in the area of its external thread 6 in a ring-shaped manner, in the jawbone 38 afflicted by periimplantitis and infested with bacteria.

The treatment element 30, 30' includes a base body 40, substantially designed as a body in the form of a cylindrical casing, whose end face 42 forming the contact surface 32 is placed onto the upper end face or end edge 34 of the post part 2. Furthermore, to increase the mechanical stability, a connection stud 43 is additionally moulded onto the base body 40, whose contour and geometrical parameters are adapted to the receiving duct 12 in the post part 2 and which can be pushed into the latter, thus enabling a reliable positioning and temporary fixation with the connection stud being pushed in.

In the interior of the base body 40 and coaxially therewith, a central inner duct 44 is provided. The treatment element 30 of the variant according to FIG. 6 is configured for use of the screw connection during the intended treatment phase, and accordingly, a connecting screw 46 is guided in the inner duct 44 in this variant. The screw thread 48 of the connecting screw 46 engages into the screw thread 20 provided inside the post part 2. Contrary to the connecting screw 18 provided for connecting the actual abutment 4 with the post part 2, the connecting screw 46 is not designed for a high mechanical load-bearing capacity and longevity of the produced screw connection; the connecting screw 46 is rather based on other design criteria, taking into consideration in particular the course of treatment explained in the following, wherein the connecting screw 46 and, with it, the post part 2, shall serve as electrode for the current impulses. Consequently, the connecting screw 46 is made of an electrically conductive material, in particular of a metal, such as, for example, titanium.

In the variant according to FIG. 7—which, otherwise, is substantially of identical construction—, the treatment element 30' is, in contrast, configured for a plug-in connection with the post part 2. For this purpose, in this variant, an electrical contacting element 49 is guided and preferably carried so as to be displaceable in its longitudinal direction, in the inner duct 44. In the design and spatial configuration of the electrical contacting element 49, the course of treatment explained in the following has also been taken into account, wherein the electrical contacting element 49 and, with it, the post part 2, shall serve as electrode for the current impulses. Therefore, in this variant, the electrical contacting element 49 is made of a suitably electrically conductive material, in particular of a metal, such as, for example, titanium, and is carried and guided in the inner duct 44 in such a manner that, when it is completely pushed into the inner duct 44, its needle tip 50 hits the bottom 52 or another region of the inner duct 44, thus making a reliable electrical contact with the post part 2. Alternatively, the electrical contacting element 49 can also be designed in its end region as a spreadable resilient element making a reliable electrical contacting on the lateral inner walls of the inner duct 44.

The treatment element 30, 30' is designed for feeding a cleaning liquid, which, among others, may also have the effect of killing germs or bacteria, into the space area 36. For this purpose, the base body 40 is provided with a plurality of media ducts 56, which are connected, on the inlet side, with a supply or feeding system for the treatment liquid. In the exemplary embodiment, the media ducts 56 are formed by grooves 59 moulded into an annular body 58 surrounding the base body 40. The annular body 58 is pushed onto the base body 40, so that the grooves 59 are closed towards the inside by the outer casing of the base body 40 and, thus, form a duct system made up of the media ducts 56. Alternatively, the media ducts may, of course, also be moulded directly into the base body 40 in another manner.

In the immediate vicinity of the contact area of the end face 42 of the base body 40 with the end edge 34 of the post part 2, the duct system formed by the media ducts 56 includes a plurality of outlet openings 60, of which FIG. 6, 7 each show only two, for better clarity. In the exemplary embodiment, each media duct 56 is provided with an outlet opening 60. Cross-section and number of the outlet openings 60 can, however, also be adapted to individual specifications. For example, a single outlet opening might be provided, forming, for example, an annular gap on the entire periphery between the end face 42 and the end edge 34. Alternatively, a plurality of outlet openings 60 may be provided, which may be arranged uniformly around the base body 40, in particular viewed in the peripheral direction of the base body 40. Alternatively, only one media duct 56 with one associated outlet opening 60 can be provided, which is preferably individually positionable and thus designed for a localized discharge of treatment liquid in a limited space area.

The outlet openings 60 of the duct system formed by the media duct(s) 56 exit in the immediate vicinity of the end face 42 and, thus, immediately above the space area 36, so that medium flowing out of the outlet openings 60 gets more or less directly into the space area 36 situated therebelow. Through this embodiment of the base body 40, which is considered as such as an independent inventive aspect, the treatment element 30, 30' thus forms a duct system, with which a treatment liquid can be introduced, in a purposeful and efficient manner, directly into the space area 36 needing treatment.

In addition, the treatment element 30, 30' is also specifically configured as an electric system. As a design principle, it is in particular provided to make it possible to charge the medium carried in the media ducts 56, in particular the salt solution carried therein, with current impulses in a pulsed manner. The treatment element 30, 30' is designed for producing the current flow provided for the purpose of cleaning the inserted implant part 2 in a specifically localized manner in the space area 36 needing treatment. The treatment element 30, 30' is configured according to the design principle that the electric current is fed to the inserted implant part 2 and that the latter can be used as electrode. For this purpose, the treatment element 30, 30' comprises a first conduction element 62, forming an electric current path and being electrically connected via the connecting screw 46 or the electrical contacting element 49 with the implant part 2, which, in turn, can be connected to a suitably chosen current or voltage source.

To form an opposite pole or the counterelectrode, it is provided to utilize the electric conductivity of the cleaning liquid carried in the media ducts 56. For this purpose, the interior of the media ducts 56 is, in turn, electrically connected with the other pole of the current or voltage source. Thus, the outlet openings 60 of the media ducts 56 form in electric terms a contact 64 or an electric contact point, via which the current flow into, or out of, the implant part 2 is affected. With this utilization of the outlet openings 60, positioned in the immediate vicinity of the space area 36 needing treatment, as an electric contact 64, it is achieved that the electric current applied for the purpose of treatment and cleaning can flow through the surface zone of the inserted implant part 2 afflicted by the bacteria and, from there, as directly as possible, i.e. in particular without making any "detours" through further body tissue or the like, to the contact surface 64 or the contact point. Therefore, the media ducts 56, inclusive of the electrically conductive cleaning liquid carried therein and the corresponding connection elements, form in the exemplary embodiment a second conduction element 66, forming an electric current path to the contact 64 arranged on the end side.

Alternatively, however, the second conduction element 66 could also be designed in the manner of a "conventional" electrode, in particular as an electrically conductive needle-like element made of metal. This electrode could in particular be mounted on the base body 40 so as to be shiftable in a longitudinal direction substantially parallel to the central axis of the base body 40. To form this electrode or an additionally provided third electrode, as required, which can be provided, for example, for locally generating an electric field, for example for strengthening of the field, a suitably shaped further metallic body may additionally be provided. The treatment element 30, 30' can also be designed without the media ducts, it being possible that the counterelectrode and, thus, the second current path, are formed exclusively by means of the metallic body. In this case, the contact 64 is formed by the end-side free surface of the respective electrode body.

The positioning of the outlet openings 60 and/or the end-side contact surface of the metallic body ensures, furthermore, that the contact surface 64 of the second conduction element 66 formed by them is positioned at a distance of at least 1 mm and of maximally 10 mm from the central longitudinal axis of the dental-implant part 2, viewed in lateral direction.

The positioning of the outlet openings 60 and/or the end-side contact surface 69 of the metallic body 68 ensures, furthermore, that the contact surface 64 of the second conduction element 66 formed by them is positioned at a distance of at least 1 mm and of maximally 10 mm from the central longitudinal axis of the dental-implant part 2, viewed in lateral direction.

The base body 40 of the treatment element 30, 30' can be made of an insulating material, such as, for example, a ceramic or synthetic material. In the exemplary embodiment, it is, however, made of metal, namely titanium. To guarantee a reliable electric insulation of the components against each other, its end face 42 forming the contact surface to the dental-implant part 2 is provided with an insulating coating 70 and, thus, configured in an electrically insulated manner. Furthermore, the annular body 58 is made of an insulating material, such as, for example, a ceramic.

In an alternative embodiment, which is not otherwise specified or shown, a non-sealing connection can also be provided when placing the base body 40 onto the end edge 34 of the post part 2. This makes it possible during the treatment phase that the treatment or cleaning liquid provided enters the interior of the post part 2 so that said interior, if required, may also be cleaned.

Figure 8:
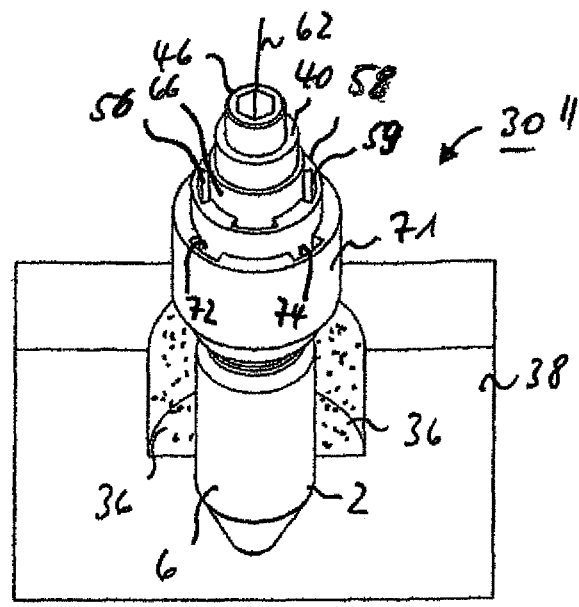

In an alternative embodiment, the treatment element 30", as shown in FIG. 8 in a perspective view, is provided with another duct system, which may be provided, for example, as a return duct for the cleaning liquid, as a separate feeding line for introducing a media mixture, or else as a suction duct. For this purpose, the annular body 58 is in this embodiment surrounded by another annular body 71, into which also grooves 74 are moulded on the inside for forming additional media ducts 72.

Figure 9:
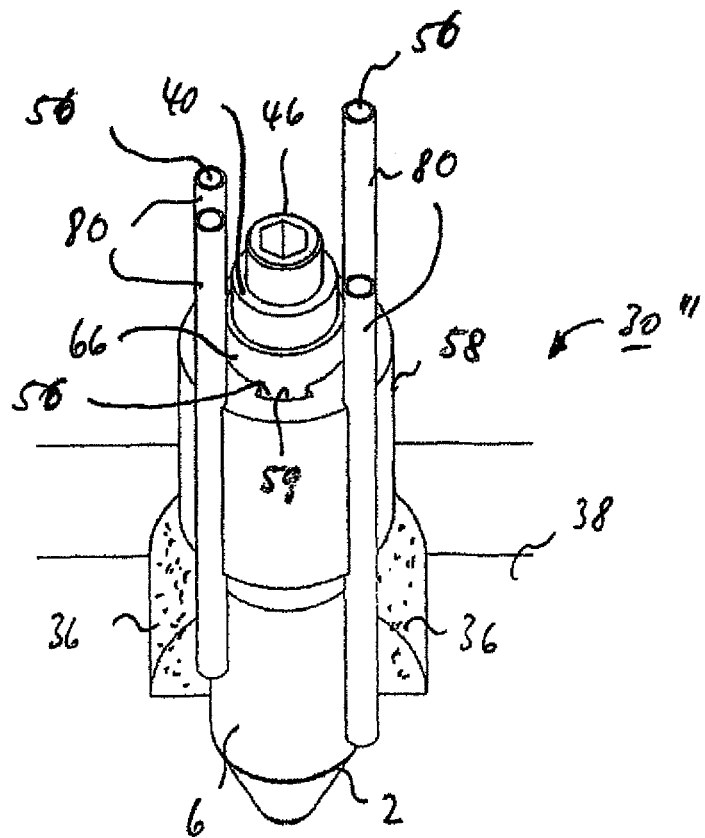
Figure 10:
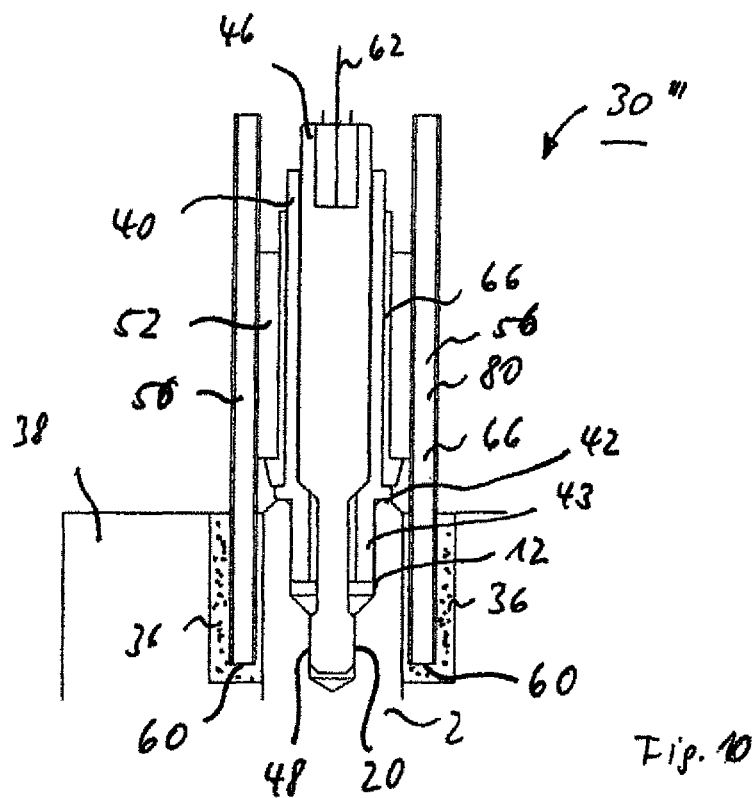
FIG. 10 shows a longitudinal section of the treatment element according to FIG. 9.

In the above-explained embodiments, the media ducts 56 and/or the conduction elements 60, 66 are designed in a substantially integrated construction and guided inside the base body 40 or inside the annular body 58, 71 connected with the latter. Alternatively or additionally, however, some or all of the media ducts 56 and/or the conduction elements 60, 66 can also be arranged on the outside of the base body 40 and connected with the latter via suitable holding elements. This configuration is shown in the exemplary embodiment in a perspective view according to FIG. 9 and in a longitudinal sectional view according to FIG. 10. In addition to the already explained components, the treatment element 30''' shown there is provided with duct elements 80 arranged on the outside of the annular body 58 so as to be shiftable in longitudinal direction. Said duct elements 80 can be designed, analogously to the media ducts 56, in the manner of hollow needles or the like, and can be charged with cleaning liquid and can additionally serve as a conduction element 66. Alternatively, however, they can also be designed metallically in the manner of electrodes and connected in an electrically suitable manner with the current or voltage source. In addition, the exemplary embodiment according to FIG. 9 shows a variant, in which, in addition to the media ducts formed by the externally arranged duct elements 80, integrated media ducts 56, formed by grooves 59 in the annular body 58, are also provided.

Figure 11:
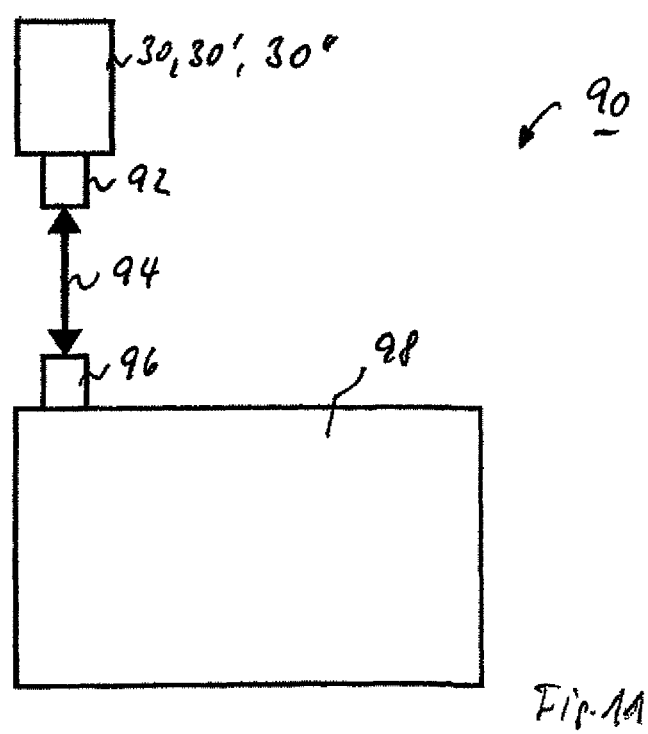
FIG. 11 shows systematically a treatment system configured for use of the treatment element.

The treatment element 30, 30', 30", 30''' is preferably used in a treatment system 90, as shown in FIG. 11. The treatment system 90 is provided for an inserted dental-implant part or post part 2 and comprises the treatment element 30, 30', 30", 30''' and, in addition thereto, a connection element 92 between the treatment element 30, 30', 30", 30''' and a hose package 94, a plug-in connection 96 between the hose package 94 and a supply and control unit 98 arranged outside the patient's mouth. This supply and control unit 98 contains an electric supply, which is able to apply a voltage and/or make a current flow between the electrode in the post part 2 and another electrode, which may be situated in the treatment element 30, 30', 30", 30''', the plug-in connections 96, the hose package 94 and/or the supply and control unit 98. This electrode includes an electrical conductive contact point to the media/electrolytes.

This voltage or current can be applied to the two electrodes as a direct voltage/current, with the polarity in both directions, or as an alternating voltage. If the voltage is an alternating voltage, it can have the shape of a sine, a triangle, a rectangle or any imaginable superimposition of these shapes, with different frequencies. Furthermore, this alternating voltage can be superimposed by a direct voltage. It is also possible to use a pulsating direct voltage. To generate an electric field, a third, electrically insulated electrode can be provided, preferably accommodated in the treatment element 30, 30', 30", 30'''.

In addition to that, the supply and control unit 98 contains reservoirs for at least two liquids or electrolytes, which can be conveyed into the treatment element 30, 30', 30", 30''' via pumps and via one or several valves or valve units simultaneously (mixingly) or one after another via the hose package 94. In a particularly favorable case, the supply and control unit 98 also contains a suction device, with which the liquids or electrolytes fed via the treatment element 30, 30', 30", 30''' can be sucked off after use. In a particularly favorable embodiment, the supply and control unit 98 also contains a $CO_2$ processing device for water or other liquids/electrolytes. For optimizing the process, a media temperature control can also be integrated into the supply and control unit 98.

The hose package 94 and the plug-in connections 96 are designed such that they are able to guarantee the current flow and the media flow. Complete equipment would in particular comprise three electric ducts and two liquid/electrolyte ducts.

The electrodes may be made of the same material as the post part 2. As the post parts 2 are preferably made of titanium or a titanium alloy, it is preferred to make the other electrode(s) of another metal. Titanium and metals similar to titanium mostly form a protective oxide layer acting as an insulator when anodically energized. In order not to limit the current flow through such an oxide layer, in case of a cathodic energization of the post part 2, it is advantageous to use, as a counterelectrode, a metal which forms hardly any oxide layer or none at all. In a particularly favorable case, this electrode corrodes neither through contact with the media/electrolytes nor under application of a voltage or current. Preferably, this electrode is made of gold, platinum, palladium.

Should the interior of the inserted implant/post part 2 also be contaminated and, consequently, be cleaned, it is possible to rinse the interior with the medium and charge it with current separately or together.

The conduction elements may also be designed in the form of a flexible or firm diaphragm, which does not allow any liquids to pass, but only the ions present in the electrolyte. In such an embodiment, preferably one of the current paths exits in the interior of the post part 2 and continues past the contact surfaces 32 which, in this case, seal only partially or not at all, up to the outer surface of the post part 2.

The treatment liquid intended for the guidance of the method is in a particularly advantageous embodiment suitably chosen and composed in view of the above-mentioned aspects. The choice and composition of the basic constituents of the treatment liquid are chosen in particular in view of the intended function, i.e. application of an electric current in the space area of the surface needing treatment, it being in particular ensured that the electric conductivity of the treatment liquid is sufficiently high for this purpose. This shall be ensured in particular by a chosen sufficiently high ion density in the treatment liquid. For this purpose, a metallic salt, preferably in aqueous solution, is provided as a basic constituent of the treatment liquid. Said metallic salt supplies the ions for the transport of current and, in addition, the conversion products arising after the respective electrode reaction can also possess suitable biochemical effects. By specifically choosing a sufficiently high electric conductivity, it shall be ensured that during the performance of the cleaning method at the inserted implant the current flows through the treatment liquid and, thus, through the parts and components needing treatment, but not through the patient's body tissue, so that a risk for the patient through an unwanted current flow through soft tissue, bones, blood, and/or other body materials can be minimized. The electric conductivity of the treatment liquid should, if possible, amount to a multiple of the electric conductivity of blood, bones, soft tissue, fatty tissue, or other body materials.

Consequently, the following conductivity values are in particular taken into consideration in the choice and composition of the basic constituents of the treatment liquid (the electric conductivity a being indicated in the usual unit mS/cm):

Skin: 0.03-0.1 mS/cm
Bone: 0.06-0.2 mS/cm
Fatty tissue: 0.20-1.0 mS/cm
Muscular tissue: 0.80-2.5 mS/cm
Blood: approx. 6.7 mS/cm
Other body liquids: approx. 15 mS/cm To keep the risk potential for the patient suitably low and to restrict the current flow to the desired regions, the electric conductivity should, therefore, amount to at least twice, preferably five times, particularly preferably ten times the conductivity of other body liquids. Therefore, the electric conductivity of the treatment liquid should have a value of at least 30 mS/cm, preferably at least 75 mS/cm and particularly preferably at least 150 mS/cm. In comparison with blood, this means that the electric conductivity of the treatment liquid preferably amounts to at least approx. five times, preferably at least approx. ten times and particularly preferably at least approx. twenty times the conductivity of blood. Measurements have shown that, when applying a treatment liquid chosen in this way, the electric voltage to which the body tissue, the blood, the body liquids, etc. are exposed, is lower than 6 V, preferably lower than 3 V, particularly preferably lower than 1.5 V, so that damages for the patient can securely be excluded, as the voltages are kept low. To achieve such a conductivity, in particular the ion concentration in the treatment liquid and in the basic constituents forming the latter are chosen sufficiently high; for this purpose, caustic solutions, acids, salts, and/or other ion-forming substances or compositions of matter can be used.

The choice and composition of the basic constituents of the treatment liquid take into consideration to a particularly high degree that the cleaning or biofilm-detaching effect of the electrolytic treatment of a contaminated implant surface is based on a combination of several causes, which should be made use of, if possible, complementarily to each other. On the one hand, gases or gas bubbles may form, when the current flows through the electrolyte, preferably in the area of the electrodes, which gases or gas bubbles have a detaching (mechanical) effect on the biofilm. These gases develop immediately at the implant surface serving as an electrode and, thus, between said implant surface and the biofilm. The growth rate and maximum size of the developing gas bubbles influence the detachment process.

The second reason for the implant-cleaning or biofilm-detaching effect of the electrolytic process is the decomposing, destroying, and dissolving effect of the electrolytically created substances or compositions of matter on the adhesion of the biofilm on the implant surface, i.e. on the gluing or anchoring mechanism.

The third reason for the cleaning or detaching effect of the electrolytic process is based on material-eroding effects on the implant material, through which component parts or particles of the implant properly speaking are extracted therefrom in its surface area.

The fourth reason for the cleaning or detaching effect of the electrolytic process is based on the formation of an oxide layer of metallic implants, which allow this. In this case, metal atoms of the metallic basic material penetrate the possibly already existing oxide layer due to the applied electric voltage and react with substances of the electrolyte (mostly oxygen=>formation of metal oxide). In metals which do not form an oxide layer or do not form a mechanically stable oxide layer, non-oxidic compositions of matter (mostly salts) may also arise, which then get into solution.

The basic constituents provided for forming the treatment liquid are suitably chosen and combined with each other in view of these effects. Furthermore, it is taken into account as a fundamental design target that no toxic effects or effects which are hazardous or disagreeable to a patient in another manner should occur, so that the treatment liquid is also suitable for being applied on the inserted dental implant, i.e. in the patient's mouth. In the exemplary embodiment, the basic constituents provided are at least one salt, on the one hand, and one acid, on the other hand, preferably diluted with water, whose choice and composition depends in particular on the above-mentioned criteria. It is particularly preferable to provide, as an acid, phosphoric acid, citric acid, malic acid, ethanoic acid, lactic acid, carbonic acid, or a combination thereof. Alternatively or additionally, it is particularly preferable to provide, as a salt, sodium, calcium, aluminium, magnesium, or potassium iodide, chloride, nitrate, carbonate, or hydrogen carbonate, and/or ammonium chlorite, nitrate, or iodide, or a combination thereof.

Furthermore, it is taken into account that the intended electrolytic process can optionally be carried out with anodic or cathodic switching of the post part. Consequently, a differentiation is made in the following between an anodic reaction and a cathodic reaction.

In an anodic reaction, i.e. with an anodic switching of the post part 2, the anions present at the anode in the treatment liquid are generally oxidized through the withdrawal of electrons. This may lead to an immediate reaction with the material, in particular to the formation of an oxide layer and/or a salt with the material of the implant. Bone implants and, therefore, also the post part 2, mostly consist of titanium, zirconium, tantalum, or of alloys of these metals. Furthermore, other metals are added by alloying. These metals or metal alloys possess in most cases a high degree of oxide-layer formation. This oxide-layer formation has a passivating effect on the surface, with the consequence that the anodic reaction of these metals or metal alloys is prevented or at least very strongly reduced. As the biofilm mostly contains compounds with oxygen, it is in most cases not possible to prevent this passivation. Should the post part be switched anodically, the detaching cleaning effect is, therefore, mostly limited to the oxide-layer formation. With higher operating voltages of, for example, more than 10 V, it could be proved by extensive examinations that a material-removing process is possible, but that the latter involves a strong development of heat. This development of heat may lead to the undesired necrosis of the bone. Furthermore, the accompanying removal of material also changes the properties of the original implant surface in an undesired manner.

As an exception therefrom, it has surprisingly turned out that with a basic material of the post part 2 containing aluminium as an alloying constituent (for example with titanium grade 5, which contains approx. 6% aluminium and 4% vanadium), an anodic energization of the post part 2 is possible without the process being too greatly impeded by the formation of an oxide layer. Therefore, depending on the composition of the treatment liquid, chlorine gas or iodine gas or else $CO_2$ can be generated directly on the surface of the post part 2 and can thus be made usable immediately for the intended detachment of the biofilm. For such a guidance of the method, the treatment element 30 is particularly advantageously provided with a conductive surface coating, for example of DLC (diamond-like carbon), a metal, a conductive synthetic material, or an electrically conductive ceramic.

It has turned out to be particularly advantageous that, with a basic material titanium grade IV or titanium grade V of the post part, by adding $CO_2$ to the treatment liquid, a formation of $CO_2$, Cl and/or I is possible, enabling a current flow of longer duration, in spite of the oxide layer forming under anodic energization.

For the above-mentioned reasons, the post part 2 is, however, in general preferably switched cathodically during the treatment with the treatment liquid. In this case, positively charged ions (cations) wander to the surface of the post part 2. These ions can be in particular $H^+$ ions, metal ions or long-chain hydrocarbon ions, e.g. from ionic liquids. The salt provided as a basic constituent for the treatment liquid is in this case particularly purposefully chosen in view of the properties of the cations which shall promote the above-mentioned process or make it possible in the first place. To generate as high an electric conductivity as possible, small ions ($H^+$ ions or metal cations) are particularly suitable, which, in addition, in the manner of another particularly favorable effect, are able, in a relatively easy manner, to penetrate the possibly existing biofilm. $H^+$ ions are reduced to elementary hydrogen H on the cathode formed by the post part 2. This generates a formation of bubbles. Another cathode reaction is the precipitation of elementary metal. Most metals, however, would precipitate as a metal deposit covering the whole area. This would be an undesired effect, because this coating would have unfavorable adhesion properties and unfavorable chemical (electrochemical and biochemical) properties.

For the above-mentioned reasons, preferably metals whose cations do not involve any biological risk potential for the patient and which in the elementary state chemically react as strongly as possible with water in the electrolyte are provided for the cathodic reaction on the implant surface. Alkali metals, noble metals and/or aluminium react upon the electrolytic reduction on the cathode immediately with the surrounding water and form elementary hydrogen and its metal cations and $OH^-$ ions. This means that hydrogen bubbles and the hydroxide of the used metal ions form. Through the combination of these components, it is, therefore, achieved, in addition to the detaching effect of the arising hydrogen, that the metal hydroxide has an antibacterial effect and a diluting or dissolving influence on the biofilm or the latter's adhesion mechanism.

To avoid incompatibilities with the body tissue, in particular the metal cations produced naturally in the body (e.g. potassium and/or sodium ions) are particularly preferred as metal cations. Furthermore, calcium, magnesium and/or aluminium ions are also suitable. The salt provided as a basic constituent for the treatment liquid is, therefore, particularly preferably a salt of these metals, in particular because these metal cations can anyhow exclusively be made available in the form of a salt, e.g. dissolved in water.

These metallic salts can be compounds of the above-mentioned metals with a suitable halogen, for example with sulphur, phosphor, nitrogen, fluorine, chlorine, iodine, bromine, hydrocarbon, oxygen, boron, or other nonmetals. The halogen is advantageously suitably chosen considering the principle "the larger the anion, the lower the electric conductivity" and in view of the generally desired high electric conductivity. Furthermore, preferably only substances influencing neither health nor the periimplantary tissue are taken into consideration as anion. Furthermore, it has to be taken into account that disagreeable smells or taste compounds are unwanted. For these reasons, sulphur anions or anions containing sulphur in combination with oxygen or other elements are considered as rather unsuitable. This also applies to fluorine, bromine, nitrogen, and boron ions, possibly also in combination with other elements.

In contrast to that, phosphates, phosphate ions and hydrogen phosphate ions mostly have hardly any detrimental effect or none at all. Chlorine ions or ions containing chlorine mostly have an antibacterial effect. Should the chlorine ion, however, be electrolytically oxidized and be present in water in the elementary state, hydrochloric acid and hypochlorous acid will form. It is true that, in combination with the cathodically generated hydroxide, this would lead to a neutralization, but examinations have shown that the chlorine arising on the counterelectrode to the implant (anode) escapes from the electrolyte to a great extent in the form of gas. If it is not possible to suck off the chlorine completely during the treatment, severe cauterizations in the lungs and/or the mucous membranes may result. In this case, one has to balance whether the benefit for the patient or the latter's endangerment is greater.

With regard to the phosphates of aluminium, potassium, sodium, calcium, or magnesium, it must, furthermore, be noted that their dissolubility in water is so low that a sufficient electric conductivity of the electrolyte is not guaranteed (these phosphates are, however, very well suited as additives of the electrolyte for buffering the pH-value). Although chlorides of the four above-mentioned metals would have a sufficient dissolubility in water and a good cleaning and killing effect on the biofilm, they cannot be considered as the optimum. In case of nitrates and/or nitrites, an endangerment of the patient through the formation of NO gases has to be expected. For this reason, the use of nitrites or nitrates is not advisable.

In view of the above-mentioned design targets, in particular for a particularly good compatibility for the patient, iodine is provided in a preferred embodiment as halogen. It is particularly advantageous that iodine salts of potassium and of sodium are naturally present in the human body. Through the oxidation of iodine ions on the anode, first of all elementary iodine develops, which can dissolve in a sodium-iodide/potassium-iodide solution. An iodine-potassium-iodide solution or an iodine-sodium-iodide solution will result thereby. Both solutions are strong disinfectants, which have proved themselves in human medicine.

Pure solutions of sodium iodide or potassium iodide or a mixture of the two entail, however, the possible disadvantage of the formation of sodium hydroxide and/or potassium hydroxide and the resulting increase of the pH-value. It could, in fact, quite generally, be considered as a problem of the above-mentioned formation of metal hydroxide that a metal hydroxide increases the pH-value of the electrolyte. Such an increased pH-value and the developing caustic solution of the dissolved metal hydroxide might have an undesired influence on the surrounding tissue in the patient's mouth and in particular, on the bone. Furthermore, adjacent teeth might be damaged. Furthermore, the formation of hydroxides might lead to their precipitation on the post part 2 or generally on the component part needing treatment, due to their very low water solubility, thus impeding the further current flow and, thus, the process as a whole. At best when using a calcium salt in the treatment liquid, the developing calcium hydroxide, which is present in the bone material, could be integrated into the bone; calcium is, therefore, a particularly preferable constituent of the salt. To compensate these undesired influences, the treatment liquid contains the acid as another basic constituent in the manner of a pH-buffer or pH-reducer.

The acid, for its part, is chosen purposefully, in the manner of a design criterion, in such a way that it does not endanger, if possible, the patient or the periimplantary tissue, but, on the one hand, neutralizes the hydroxide (and prevents, if possible, an increase of the pH-value to more than 7), whereby, on the other hand, the reaction products should serve for the actual target of cleaning the implant body and removing the biofilm. As mineral acids, phosphoric acids and/or phosphate acids are preferred for that purpose. For reasons of hazards to health and/or to the bone/tissue, their concentration should be limited to maximum values of 30% or preferably, of 10% to 20%. A particularly preferable acid, which is also considered as a mineral acid and which has a particularly positive effect on the overall target of killing and cleaning, is, on the other hand, carbonic acid. The usable quantity of the latter is, however, limited through its relatively low solubility in water.

Contrary thereto, organic acids, similar to mineral acids, provide pH-value-reducing and hydroxide-neutralizing $H^+$ ions. As, in addition, they do not produce any damages, or at most slight damages, in the tissue or in the patient as a whole, such organic acids are most particularly preferred as a basic constituent of the treatment liquid. Organic acids are, for example, alkane acids, fruit acids, carboxylic acids as well as hydroxy carbonic acids. α-hydroxy carbonic acids have turned out to be particularly suitable acids. In particular, the particularly preferable acids lactic acid, citric acid, and malic acid have no effects hazardous to health on the patient in general or on the periimplantary tissue. Especially on implants greatly covered and contaminated with a biofilm, on which tartar has also developed, a good cleaning success was achieved with relatively low dosages of ethanoic acid. Other acids, which have the cleaning as well as the bactericidal effect, but, for health reasons, are not harmless, would be fumaric acid, gluconic acid, glycolic acid, salicylic acid, mandelic acid, tartaric acid, oxalic acid, and formic acid.

When the hydroxide ion OH' is neutralized with the corresponding $H^+$ ion of an acid, the metallic salt of the used acid of the corresponding metal hydroxide will additionally be produced. The intended use of the acid is, therefore, not only advantageous for buffering the pH-value, but, in addition, contributes to the conversion of the relatively little water-soluble hydroxide into relatively well water-soluble salts, thus preventing the precipitation of unwanted deposits, detrimental to the process, on the component part needing treatment. The above-mentioned salts are in particular used when combining the above-mentioned preferred materials, among other, also in the field of medicine. During the neutralization of the potassium, sodium and/or calcium hydroxide with lactic acid, potassium lactate (possessing a broad-spectrum antimicrobial effect), sodium lactate or calcium lactate arises. It, however, the produced hydroxides are neutralized with citric acid, citrates of potassium, sodium or calcium will arise. Especially in the case of sodium citrate, this is particularly advantageous, as it prevents blood coagulation. This is particularly advantageous, because blood escaping during the process and coagulating on the implant surface might impede the ion wandering to the implant surface and, thus, the continuation of the treatment process as a whole.

Contrary thereto, in case of a neutralization of the hydroxides with malic acid, malates of the respective cation arise, which also have favorable effects on the process. In case of a neutralization of the hydroxides with ethanoic acid, acetates of potassium, sodium and/or calcium arise, which also have a favorable effect on the process.

Lactates, citrates, malates, and/or acetates of potassium, sodium and/or calciums all possess an acid-regulating effect and are so compatible that according to the present EU regulations concerning food additives, their use is not subject to any quantitative limitation.

When using acids in the electrolyte in combination with iodides and/or chlorides of sodium, potassium, magnesium, aluminium, and/or calcium, it has surprisingly turned out in the electrolytic application that the direct reduction of the $H^+$ ions influences the formation of bubbles so positively that the biofilm comes off clearly more quickly and better. At a high generation rate, a multitude of relatively small bubbles develop, which due to their relatively small size are able to detach the biofilm as a whole and not only locally from the surface underneath it. In this way, the biofilm is preferably detached as a whole or in relatively large coherent pieces instead of a multitude of smaller fragments, which entails a clearly improved cleaning effect.

Instead of metal cations, ammonium cations can also be used. In this case, there exists, however, the risk that in the electrolytic process, other ammonium compounds (e.g. ammonia) are generated. This constitutes a risk for the patient and is also perceived through a very disagreeable taste and smell.

What is claimed is:

1. A treatment element for use with a dental-implant part anchored in a patient's jawbone, said treatment element comprising:
    a base body having a connection system adapted to the dental-implant part for mechanical connection of the base body with the dental-implant part, and at least one media duct for conducting a cleaning liquid,
    said base body comprising a first conduction element and a second conduction element electrically insulated from the first conduction element, said first conduction element forming an electric current path and being connectable with the dental-implant part, said second conduction element forming an electric current path to a contact arranged on an end side of the second conducting element, said contact being positionable in a region proximate to the dental-implant part, wherein the second conduction element is formed by one or more of the at least one media duct.

2. The treatment element of claim 1, wherein the connection system comprises a connecting screw for threaded engagement in a threaded bore of a post part of a two-part or multi-part dental-implant system.

3. The treatment element of claim 2, wherein the connecting screw is connected with the first conduction element in an electrically conductive manner.

4. The treatment element of claim 1, wherein the second conduction element is constructed as an electrode or conduit mounted on the base body so as to be shiftable in a longitudinal direction substantially parallel to a central longitudinal axis of the base body.

5. The treatment element of claim 1, wherein the second conduction element is fixed on the base body so that said contact is positionable at a distance of maximally 10 mm to a central longitudinal axis of the dental-implant part, viewed in lateral direction.

6. The treatment element of claim 1, wherein a contact surface of the base body with which the base body contacts the dental-implant part when connected to the dental implant part is constructed electrically insulated.

7. A treatment system for a dental-implant part comprising:
    a treatment element comprising a base body,
    said base body having a connection system adapted to the dental-implant part for mechanical connection of the base body with the dental-implant part, and at least one media duct for conducting a cleaning liquid, said at least one media duct being arranged integrated in or on the base body and having an outlet opening positioned at a distance of not more than 10 mm to the dental implant part when the base body is placed on the dental implant part;
    a connection element arranged between the treatment element and a hose package; and
    a supply and control unit connected on a medium side with the treatment element via the hose package,
    wherein said base body comprises a first conduction element forming a first electrode, which forms an electric current path and is connectable with the dental-implant part, and a second conduction element forming a second electrode electrically insulated from the first conduction element, said second conduction element forming an electric current path to a contact arranged on an end side of the second conducting element, said contact being positionable in a region proximate to the dental-implant part, wherein the first and second conduction elements are connected with a current or voltage source in an electrically conductive manner,
    wherein the second conduction element is formed by one or more of the at least one media duct.

8. The treatment system of claim 7, wherein the current or voltage source is configured for pulsatingly charging the first and second electrodes with current or voltage.

9. The treatment system of claim 7, configured for an operating voltage applied on the first and second electrodes of up to 30 V.

10. The treatment system of claim 7, further comprising a feeding system for a cleaning liquid connected to the treatment element.

11. The treatment system of claim 10, further comprising a cleaning liquid, wherein the cleaning liquid is water mixed with at least one acid and/or at least one salt.

* * * * *